United States Patent [19]

Labaw et al.

[11] 4,104,472

[45] Aug. 1, 1978

[54] IMIDAZOLEMETHYLPHOSPHONIUM SALTS

[75] Inventors: Clifford Steven Labaw, Philadelphia; Robert Lee Webb, West Chester; George Robert Wellman, Warminster, all of Pa.

[73] Assignee: SmithKline Corporation, Philadelphia, Pa.

[21] Appl. No.: 800,150

[22] Filed: May 24, 1977

Related U.S. Application Data

[63] Continuation-in-part of Ser. No. 767,083, Feb. 9, 1977.

[51] Int. Cl.$^2$ .............................................. C07F 9/65
[52] U.S. Cl. ................................... 548/337; 548/342; 548/343
[58] Field of Search ................................ 548/337, 343

[56] References Cited

U.S. PATENT DOCUMENTS

| | | | |
|---|---|---|---|
| 2,844,582 | 7/1958 | Raley, Jr. | 548/337 |
| 3,185,699 | 5/1965 | Sherlock | 548/343 |

OTHER PUBLICATIONS

Balaban et al., Chem. Abst., 1927, vol. 21, pp. 3614–3615.
John, Chem. Abst., 1936, vol. 30, columns 2565–2566.
Oliver et al., Chem. Abst., 1973, vol. 78, No. 136177f.

*Primary Examiner*—Natalie Trousof
*Attorney, Agent, or Firm*—William H. Edgerton

[57] ABSTRACT

New imidazolemethylphosphonium salts having a degradable group at the 2-position which are useful intermediates for preparing histamine $H_2$ antagonists.

7 Claims, No Drawings

IMIDAZOLEMETHYLPHOSPHONIUM SALTS

This application is a continuation-in-part of Ser. No. 767,083, filed Feb. 9, 1977.

The object of this invention is a new series of imidazolemethyltriphenylphosphonium salts which are useful intermediates for preparing end products having medicinal activity especially histamine $H_2$ antagonists such as cimetidine which are known to inhibit gastric acid secretion (U.S. Pat. No. 3,950,333). Another aspect of this invention is the chemical methods of using this class of new intermediates.

The compounds of this invention are tertiary imidazolemethylphosphonium salts whose structures are characterized by having at the 2-position a group which can be easily converted to a 2-hydrogen imidazole. Illustrative of these compounds are the following:

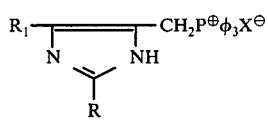
                                                      I in which:
R is trichloromethyl, tribromomethyl, sulfinic acid ($-SO_2H$), carbo-lower-alkoxy ($-CO_2R_2$) or carboxy ($-CO_2H$); and
$R_1$ is hydrogen, phenyl or lower alkyl of 1-6 carbons such as the preferred methyl;
X is any inexpensive anion as known to the art but is most conveniently a halide especially chloride, bromide or iodide. Other anions might include organic anions such as tosylate or mesylate, inorganic anions such as sulfate, phosphate or carbonate, hydroxyl or lower alkoxides such as methoxide or ethoxide;
$R_2$ is most conveniently lower alkyl corresponding to commercially available solvent alcohols such as methanol, ethanol, isopropanol, propanol or n-butanol. Therefore $R_2$ is preferably lower alkyl of from 1-4 carbon atoms.

$R_1$ is not critical to this invention and may be any inert substituent such as those mentioned above. Preferred is methyl. $\phi$ is the common designation for phenyl but other tertiary phosphonium moieties may be substituted such as mixed or straight aryl or alkyl groups. For convenience the triphenylphosphonium salts are used since the triphenylphosphine can be easily recycled for further use again in the reaction sequence described hereafter.

One skilled in the art will recognize that the imidazole ring has a basic center which can be optionally neutralized with an inorganic or organic salt to form the acid addition salts. The salts with strong mineral acids such as the hydrochloride or hydrobromide are most convenient. These are prepared by methods known to the art for forming salts. In certain cases as will be apparent from this disclosure acid is produced in situ which forms the salt directly as in the conversion to the 2-carboxylic esters or acid. At high, dry temperatures used in certain reactions described herein the salts are converted to the basic forms by the heat.

The intermediate compounds of Formula I in which R is trichloromethyl, tribromomethyl or sulfinic acid are prepared by reacting trichloroacetamidine, tribromoacetamidine or formamidine sulfinic acid respectively with a trisubstituted $\beta$-acylvinylphosphonium halide, preferably bromide or chloride, of the formula $\phi_3P^\oplus-CH=CH-COR_1X^\ominus$ in which $R_1$ and $X^\ominus$ are as defined. Such reactions and starting materials are described by Zbiral, Synthesis 11, 775 (1974) and Zbiral and Hugl, Phosphorus 2, 24 (1972). The triphenyl $\beta$-acylvinylphosphonium halides not known to the art are prepared by reacting a halovinyl alkyl or phenyl ketone with triphenylphosphine. When $R_1$ is hydrogen, the triphenyl $\beta$-formylvinylphosphonium halide is prepared by oxidation of a $\beta$-haloallyl alcohol then reaction with triphenylphosphine.

The compounds of Formula I in which R is carbalkoxy or carboxy are prepared by another aspect of this invention. The 2-trihalomethyl-4-triphenyl phosphoniumimidazoles of Formula I are reacted with an excess of the desired alcohol, preferably methanol or ethanol, to prepare the esters or with water in an inert organic solvent to prepare the carboxylic acid. The reaction is run most conveniently at ambient temperature such as room temperature but also may be run up to the reflux temperature of the reaction mixture. The reaction proceeds most often very rapidly but can also be conveniently run overnight if desired. An excess of the desired alcohol can be used or smaller amounts of the alcohol or water in an inert organic solvent such as acetonitrile, dimethylsulfoxide ethyl acetate or tetrahydrofuran can be used. Excellent yields of pure product are obtained, often quantitative.

As a preferred alternative the intermediate trihalomethyl compound need not be isolated. For example trichloro acetamidine is reacted with triphenyl $\beta$-acetylvinylphosphonium bromide or chloride in methanol solution from room temperature to the reflux temperature of the reaction mixture. The 2-trihalomethyl compound is initially formed followed by immediate reaction with methanol to produce the 2-carbomethoxy intermediate. Other carboalkoxy derivatives may also be prepared similarly.

The compounds of Formula I in which R is sulfinic acid, carboalkoxy or carboxy are converted to the desired 2-hydrogen intermediates by heating or standing until evolution of gas, sulfur dioxide or carbondioxide, is complete. Temperatures of from about $-10°-250°$ are often used. For example, the sulfinic acids decompose very rapidly in the lower range of temperature from about $-10°-120°$ while the 2-carbalkoxy and 2-carboxy containing compounds decompose at heating from 150°-250° preferably from 170°-200°. Usually the decomposition temperature of the carboxy compounds is at or above the melting point of the compound. Lower temperatures can be used by addition of finely/divided metallic salts or metals such as copper powder or copper oxide.

It will be recognized as stated above that, during the decomposition of the 2-sulfinic acid, sulfur dioxide will be evolved. If for environmental reasons this is desirable, the carboxylate route is often used to advantage since yields are good and no noxious gases are evolved.

The compounds of Formula II prepared by using the methods and intermediates of this invention are of utility for preparing histamine $H_2$ antagonists such as cimetidine by the following procedures:

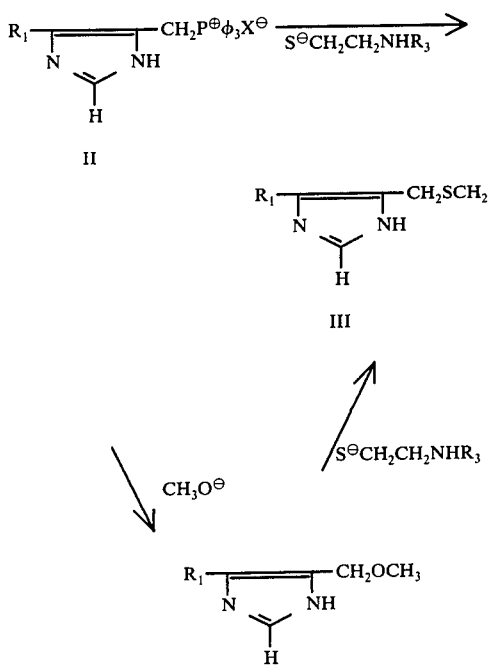

In this procedure $R_1$ and X are as described above. $R_3$ is hydrogen or

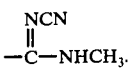

The compounds of Formula III are of utility as described in U.S. Pat. No. 3,950,333 and other related patents.

The following examples are intended to teach the operation and utility of this invention to those skilled in the art but are not intended to limit the scope thereof. Temperatures are in degrees Centigrade (C°).

EXAMPLE 1

Trichloroacetamidine (1.62 g., 0.01 mole) was dissolved in 20 ml of dry dimethylsulfoxide and 4.1 g (0.01 mole) of triphenyl β-acetylvinylphosphonium bromide in 40 ml of dimethylsulfoxide was added in one portion with stirring. The exothermic reaction mixture gradually lightened in color and was heated at 100° for 10 minutes. Evaporation of the solvent gave [(5-methylimidazolyl)-4-methyl]triphenylphosphonium bromide.

The product in this procedure was produced in poor yield relative to those produced in later examples.

EXAMPLE 2

Formamidine sulfinic acid (11.0 g., 0.1 mole) was suspended in 250 ml of dry dimethylsulfoxide and 2.4 g (0.1 mole) of sodium hydride was added. After cessation of hydrogen gas evolution 36.5 g (0.1 mole) of triphenyl β-acetylvinylphosphonium chloride was added and the mixture was stirred for one hour at ambient temperature, then heated at 100° for 10 minutes to complete the loss of sulfur dioxide. After cooling, the dimethylsulfoxide was evaporated and the residue was dissolved in 300 ml of 1:1 chloroformmethanol and the solution filtered. The filtrate was evaporated to dryness and the residue was recrystallized from chloroform-acetone to give 20 g (50%) of [(5-methylimidazolyl)-4-methyl]triphenylphosphonium chloride, m.p. 223°-225°.

The 2-sulfino intermediates are most useful without being isolated because of their ease of losing sulfur dioxide.

EXAMPLE 3

Triphenyl β-acetylvinylphosphonium chloride (3.65 g., 0.01 mole) and formamidine sulfinic acid (1.1 g, 0.01 mole) was dissolved in 50 ml of dimethylsulfoxide. 1,8-bis-(Dimethylamino)naphthalene ("proton sponge") (2.14 g, 0.01 mole) was added and the mixture warmed to 80° to complete the loss of sulfur dioxide. After cooling, evaporating the dimethylsulfoxide, precipitating the inorganic salts with chloroform, filtering, evaporating to dryness and recrystallizing the residue from chloroform-acetone, an essentially quantitative yield of [(5-methylimidazolyl)-4-methyl]triphenylphosphonium chloride was obtained, m.p. 227°-229°.

EXAMPLE 4

Triphenyl β-acetylvinylphosphonium bromide (20.6 g, 0.05 mole) and formamidine sulfinic acid (6.0 g, slight excess over 0.05 mole) were dissolved in 100 ml of dimethylsulfoxide, 1,5-Diazabicyclo[5.4.0]-undec-5-ene (DBU) (7.6 g, 0.05 mole) was added dropwise with stirring. The mixture was maintained at 80° for 20 minutes to complete decomposition and the dimethylsulfoxide was evaporated off. The residue was taken up in chloroform and inorganic salts were removed by filtration. The filtrate was evaporated to dryness and the residue was recrystallized from chloroform-acetone to give [(5-methylimidazolyl)-4-methyl]triphenylphosphonium bromide in 80% yield.

EXAMPLE 5

Triphenyl β-acetylvinylphosphonium bromide (8.0 g, 0.019 mole) was dissolved in a minimum amount of dry acetonitrile (about 100 ml) and trichloroacetamidine (4.0 g, 0.025 mole) was added in one portion. The resulting mixture was stirred at room temperature and the material which crystallized out was filtered off to give [(2-trichloromethyl-5-methylimidazolyl)-4-methyl]triphenylphosphonium bromide, 8.0 g (76%), m.p. 155°-157°.

The phosphonium bromide (15.0 g, 0.027 mole) was added to 150 ml of methanol and the resulting mixture was refluxed for three hours. The pH of the reaxtion mixture was ul. The mixture was concentrated to about 15 ml and the solid material was filtered off to give [(2-carbomethoxy-5-methylimidazolyl)-4-methyl]triphenylphosphonium bromide, 12.0 g (89%) m.p. 168°-170°.

The above prepared phosphonium salt is heated to its melting point (approximately 170°) and held at this temperature until the evolution of gas is complete. On cooling, the solid product is triturated with chloroform to give [(5-methylimidazolyl)-4-methyl]-triphenylphosphonium bromide.

Substituting ethanol, isopropanol or butanol in the reaction given the corresponding ethyl, isopropyl or butyl ester.

EXAMPLE 6

Triphenyl β-acetylvinylphosphonium chloride (36 g, 0.01 mole) and trichloroacetamidine (16.1 g, 0.1 mole) were stirred in 200 ml of methanol for one hour. The solution was heated to reflux, immediately cooled and the methanol evaporated to leave [(2-methoxycarbonyl-5-methylimidazolyl)-4-methyl]triphenylphosphonium chloride hydrochloride, 50 g of light yellow product, m.p. 170° (d). Heating this phosphonium chloride salt at 170° until evolution of gas is complete, then cooling and triturating with chloroform gives [(5-methylimidazolyl)-4-methyl]triphenylphosphonium chloride. Similarly the hydrobromide salt was obtained using 41 g of phosphonium bromide and 16.1 g of trichloroacetamidine.

Substituting for trichloroacetamidine equivalent quantities of tribromoacetamidine in these reactions gives [(2-tribromomethyl-5-methylimidazolyl-4-methyl]triphenylphosphonium bromide then upon reaction with methanol the same 2-carbomethoxy intermediate and 2-hydrogen end products.

EXAMPLE 7

Triphenyl β-benzoylvinylphosphonium bromide (4.7 g, (0.01 mole) and trichloroacetamidine 1.6 g (0.01 mole) were dissolved in 40 ml of methanol and stirred for 15 minutes at room temperature. The solution was heated to reflux, cooled and stripped to dryness. The light yellow colored solid 6.1 g, m.p. 175°(d), was [(5-phenyl-2-carbomethoxyimidazolyl)-4-methyl]triphenyl phosphonium bromide hydrochloride in a quantitative yield as the monohydrate.

EXAMPLE 8

[(2-Trichloromethyl-5-methylimidazolyl)-4-methyl]-triphenylphosphonium chloride (5.0 g, .001 mole) was suspended in acetonitrile and water (2 ml, 11 m) was added. The reaction was exothermic. The solid material went into solution and then precipitated out to give [(2-carboxy-5-methylimidazolyl)-4-methyl]triphenyl phosphonium chloride hydrochloride dihydrate, m.p. 170°(d).

Continued heating of the carboxylic acid at or above the melting point evolves carbon dioxide and give [(5-methylimidazolyl)-4-methyl]triphenylphosphonium bromide hydrochloride m.p. 240°.

EXAMPLE 9

7.3 g (0.5 mole) of β-pivaloylvinyl chloride and 8.1 g (0.05 m) of triphenyl phosphine were dissolved in 100 ml benzene and heated at reflux for 30 minutes. The mixture was cooled and filtered, washed with benzene and dried to afford 12 g of product as a white powder, mp 193°–195°.

Trichloroacetamidine (3.22 g, 0.02 mole) was added to a stirred solution of triphenyl β-pivaloylvinylphosphonium bromide (8.16 g, 0.02 mole) and methanol (50 ml). The mixture was stirred overnight at room temperature. The methanol was removed under reduced pressure to leave 11.32 g of white solid. This solid was dissolved in chloroform and the solution was filtered to remove undissolved solids. The filtrate was evaporated under reduced pressure. The residue was dried under high vacuum to give 9.6 gms (91% yield) of [(4-t-butyl-2-carbomethoxyimidazolyl)-5-methyl]triphenylphosphonium chloride as a white solid, m.p. 120°(dec).

EXAMPLE 10

The 5-tert. butyl compound from Example 9 (9 g) was heated to 180°–190° for 15 minutes and cooled to leave a product which was recrystallized from acetonitrile to give [(5-tert. butylimidazolyl)-4-methyl]triphenyl phosphonium chloride, m.p. 134°–137°(d).

EXAMPLE 11

Triphenyl β-acetylvinylphosphonium bromide (4.11 g, 0.01 mole) was added in one portion to a stirred suspension of 1.1 g (0.01 mole) of formamidine sulfinic acid in 20 ml of dimethylsulfoxide containing 0.25 g of sodium hydride. The mixture was stirred at ambient temperature for 1 hour then at 80° for an additional hour. A solution of 0.99 g (0.01 mole) of the sodium salt of cysteamine, prepared by addition of two equivalents of sodium methoxide to cysteamine dihydrochloride, in 10 ml of methanol was added and the resulting mixture was heated at 70°–80° for 4 hours. The mixture was diluted with twice its volume of water and the triphenyl phosphine was removed by filtration. The filtrate was extracted with 100 ml of toluene and with two 100 ml portions of chloroform. The chloroform extracts were combined, dried and evaporated to dryness to give 4-(2-aminoethyl)thiomethyl-5-methylimidazole in 45% yield.

(a) A solution of 17.0 g of 4-(2-aminoethyl)thiomethyl-5-methylimidazole and 11.2 g of N-cyano-N',S-dimethylisothiourea in 500 ml of acetonitrile was refluxed for 24 hours. The mixture was concentrated and the residue was chromatographed on a column of silica gel with acetonitrile as eluant. The product obtained was recrystallized from acetonitrile-ether to give N-cyano-N'-methyl-N''-[2-(5-methyl-4-imidazolylmethylthio)ethyl]-guanidine, m.p. 141°–142°.

(b) A solution of 23.4 g of 4-(2-aminoethyl)thiomethyl-5-methylimidazole in ethanol was added slowly to a solution of 20.0 g of dimethyl-N-cyanoimidodithiocarbonate in ethanol, with stirring at ambient temperature. Filtration afforded N-cyano-N'-[2-(5-methyl-4-imidazolylmethylthio)ethyl]-S-methylisothiourea, m.p. 148°–150°. The filtrate was concentrated under reduced pressure and the mixture was triturated with cold water to give a solid material which was collected by filtration and recrystallized twice from isopropanolether, m.p. 148°–150°.

A solution of 75 ml of 33% methylamine in ethanol was added to a solution of 10.1 g of N-cyano-N'-[2-(5-methyl-4-imidazolylmethylthio)-ethyl]-S-methylisothiourea in 30 ml of ethanol. The reaction mixture was set aside at ambient temperature for 2.5 hours. Following concentration under reduced pressure, the residue was recrystallized twice from isopropanol-petroleum ether to give N-cyano-N'-methyl-N''-[2-(5-methyl-4-imidazolylmethylthio)ethyl]guanidine, m.p. 141°–143°.

EXAMPLE 12

Tri-n-butylphosphine (20.2 g, 0.1 mole) is added to a solution of 10.4 g (0.1 mole) of chlorovinyl methyl ketone in 250 ml of benzene and the mixture is refluxed for 1 hour. The mixture is cooled and the precipitate material is collected by filtration and dried to give tri-n-butyl β-acetylvinylphosphonium chloride.

Triethyl β-acetylvinylphosphonium chloride is prepared as described above by use of triethylphosphine in place of tri-n-butylphosphine.

Reaction of an equivalent amount of tri-n-butyl β-acetylvinylphosphonium chloride or triethyl β-acetylvinylphosphonium chloride with formamidine sulfinic acid or trichloroacetamidine as described above gives [(5-methylimidazolyl)-4-methyl]tri-n-butylphosphonium chloride and [(5-methylimidazolyl)-4-methyl]- triethylphosphonium chloride, respectively as well as the 2-trichloromethyl and 2-carbomethoxy intermediates.

Reaction of [(5-methylimidazolyl)-4-methyl]tri-n-butylphosphonium chloride or [(5-methylimidazolyl)-4-methyl]triethylphosphonium chloride with cysteamine in the presence of sodium methoxide or sodium hydride gives 4-(2-aminoethyl)thiomethyl-5-methylimidazole.

EXAMPLE 13

Cysteamine (12.23 g, 0.13 mole) is dissolved in 100 ml of methanol and 46.5 ml of 25% wt/v sodium methoxide solution is added. After stirring at ambient temperature for 10 minutes, 0.1 mole of [(5-methylimidazole)-4-methyl]-triphenylphosphonium bromide is added. The reaction mixture is heated at reflux for 20 minutes. The solution is diluted with twice its volume of ice water and stirred. The precipitate triphenylphosphine is removed by filtration. The filtrate is extracted with chloroform which extracts are dried and evaporated to yield 4-(2-aminoethyl)thiomethyl-5-methylimidazole.

Other substituted triphenylphosphonium salts such as halides or hydroxides may be similarly converted to thioamine derivatives.

EXAMPLE 14

A solution of 48.3 g (0.1 mole) of [(5-methylimidazolyl)-4-methyl]triphenylphosphonium bromide in 250 ml of methanol is added rapidly at ambient temperature to a stirred solution of 35 ml of 25% sodium methoxide in methanol in 250 ml of methanol. The mixture is refluxed for 20 minutes then concentrated to half the volume. After dilution with 900 ml of water, the triphenyl phosphine is removed by filtration. The aqueous solution is extracted twice with 150 ml portions of benzene and then three times with 250 ml portions of chloroform. The chloroform extracts are combined, dried and evaporated to dryness to give 4-methoxymethyl-5-methylimidazole.

EXAMPLE 15

4-Methoxymethyl-5-methylimidazole as the hydrochloride (4.5 g, 0.03 mole) and 3.4 g (0.03 mole) of cysteamine hydrochloride were dissolved in a minimum amount of acetic acid and the mixture was refluxed for 18 hours. After cooling in an ice bath, the mixture was filtered to give 5.8 g (80%) of 4-(2-aminoethyl)thiomethyl-5-methylimidazole dihydrochloride salt (thioamine salt).

What is claimed is:

1. A compound of the formula:

$$R_1 \underset{N \diagdown \diagup NH}{\overline{\qquad}} CH_2 P^{\oplus} \phi_3 X^{\ominus}$$
$$\underset{R}{|}$$

in which:
R is sulfinic acid, carbolower-alkoxy or carboxy;
$R_1$ is hydrogen, lower alkyl of 1–6 carbons or phenyl; and
$X^{\ominus}$ is chloride or bromide; or its acid addition salts.

2. The compound of claim 1 in which R is sulfinic acid.
3. The compound of claim 1 in which R is carbomethoxy.
4. The compound of claim 1 in which $R_1$ is methyl.
5. The compound of claim 3 in which $R_1$ is methyl.
6. The compound of claim 5 in the form of the base.
7. The compound of claim 5 in the form of the hydrochloride or hydrobromide salt.

* * * * *

UNITED STATES PATENT AND TRADEMARK OFFICE
CERTIFICATE OF CORRECTION

PATENT NO. : 4,104,472

DATED : August 1, 1978

INVENTOR(S) : Clifford Steven Labaw, Robert Lee Webb and George Robert Wellman

It is certified that error appears in the above-identified patent and that said Letters Patent are hereby corrected as shown below:

Name of Assignee "SmithKline Corporation, Philadelphia, Pa." should read -- SK&F Lab Co., Carolina, P.R. --.

Signed and Sealed this

Tenth Day of April 1979

[SEAL]

Attest:

RUTH C. MASON
Attesting Officer

DONALD W. BANNER
Commissioner of Patents and Trademarks